United States Patent
Lee et al.

(10) Patent No.: US 10,813,969 B2
(45) Date of Patent: Oct. 27, 2020

(54) ARTIFICIAL SEBUM FILM AND METHOD OF PRODUCING SAME

(71) Applicants: Kun-Lin Lee, Kaohsiung (TW); Chung-Yu Hsieh, Kaohsiung (TW)

(72) Inventors: Kun-Lin Lee, Kaohsiung (TW); Chung-Yu Hsieh, Kaohsiung (TW)

(73) Assignee: Jola International Co., Ltd., Kaohsiung (TW)

( * ) Notice: Subject to any disclaimer, the term of this patent is extended or adjusted under 35 U.S.C. 154(b) by 297 days.

(21) Appl. No.: 15/871,997

(22) Filed: Jan. 16, 2018

(65) Prior Publication Data

US 2018/0133276 A1 May 17, 2018

(30) Foreign Application Priority Data

Jan. 25, 2017 (TW) .............. 106103047 A

(51) Int. Cl.
| | |
|---|---|
| *A61K 36/82* | (2006.01) |
| *A61K 31/232* | (2006.01) |
| *A61K 35/36* | (2015.01) |
| *A61K 31/7076* | (2006.01) |
| *A61K 31/20* | (2006.01) |
| *A61K 31/685* | (2006.01) |
| *A61K 31/575* | (2006.01) |
| *A61K 31/01* | (2006.01) |
| *A61K 36/899* | (2006.01) |

(52) U.S. Cl.
CPC .............. *A61K 36/82* (2013.01); *A61K 31/01* (2013.01); *A61K 31/20* (2013.01); *A61K 31/232* (2013.01); *A61K 31/575* (2013.01); *A61K 31/685* (2013.01); *A61K 31/7076* (2013.01); *A61K 35/36* (2013.01); *A61K 36/899* (2013.01)

(58) Field of Classification Search
CPC .. A61K 2300/00; A61K 36/82; A61K 36/899; A61K 31/01; A61K 31/20; A61K 31/232; A61K 31/575; A61K 31/685; A61K 31/7076; A61K 35/36
See application file for complete search history.

(56) References Cited

U.S. PATENT DOCUMENTS 6,342,208 B1 * 1/2002 Hyldgaard ............... A61K 8/06
424/400

* cited by examiner

*Primary Examiner* — Aaron J Kosar

(57) ABSTRACT

A method for producing an artificial sebum film is provided with in raw material component and relative ratio, 78.4%-2% of triglyceride, 1%-15% of wax and ester, 20%-35% of squalane, 0.1%-7% of free fatty acid, 0.1%-6% of phospholipid, 0.1%-10% of cholesterol ester, 0.1%-10% of cholesterol, 0.1%-10% of antioxidant and 0.1%-5% of cellular activity regulator. The invention modifies the proportion of raw material composition of the artificial sebum film to reduce the negative effect generated by oxidation, and increase the proportion of squalane, so that the skin under high pollution can restore to the normal equilibrium state. Further, antioxidants and cellular active regulators are added to prolong the oxidation time of artificial sebum film and replenish the adenosine triphosphate in the cells.

1 Claim, No Drawings

ARTIFICIAL SEBUM FILM AND METHOD OF PRODUCING SAME

BACKGROUND OF THE INVENTION

1. Field of the Invention

The invention relates to artificial sebum film and more particularly to an artificial sebum film and a method of producing same having improved characteristics.

2. Description of Related Art

The well known artificial sebum film generally has the following disadvantages: firstly, it comprises triglyceride which is easily oxidized, easy to cause change in color and odor on long-term storage, and easy to cause decomposition of free fatty acid, leading to decrease in PH; secondly, if placed in a low temperature environment, it is easy to freeze or cause release of a specific high melting point component, resulting in changes in the composition. In addition, due to the increasingly serious pollution (including PM2.5 suspended particles, UV light, high temperature and other factors), the barrier capacity of the sebum layer of residents living in highly polluted areas (such as the densely populated cities) is generally insufficient.

Based on the above content, the current artificial sebum film may have shortcomings of easy oxidation and poor stability. In addition, facing the increasing adverse environmental situation, after reaction with pollutants, the existing sebum composition will result in decrease in barrier degree to be unable to effectively protect skins.

Thus, the need for improvement still exists.

SUMMARY OF THE INVENTION

It is therefore one object of the invention to provide an artificial sebum film comprising, in raw material component and relative ratio, 78.4%-2% of triglyceride, 1%-15% of wax and ester, 20%-35% of squalane, 0.1%-7% of free fatty acid, 0.1%-6% of phospholipid, 0.1%-10% of cholesterol ester, 0.1%-10% of cholesterol, 0.1%-10% of antioxidant and 0.1%-5% of cellular activity regulator.

The above and other objects, features and advantages of the invention will become apparent from the following detailed description.

DETAILED DESCRIPTION OF THE INVENTION

An artificial sebum film of the invention comprises, in raw material component and relative ratio, 2%-78.4% of triglyceride, 1%-15% of wax and ester, 20%-35% of squalane, 0.1%-7% of free fatty acid, 0.1%-6% of phospholipid, 0.1%-10% of cholesterol ester, 0.1%-10% of cholesterol, 0.1%-10% of antioxidant and 0.1%-5% of cellular activity regulator.

A method for producing an artificial sebum film of the invention comprises, in raw material component and relative ratio, 2%-78.4% of triglyceride, 1%-15% of wax and ester, 20%-35% of squalane, 0.1%-7% of free fatty acid, 0.1%-6% of phospholipid, 0.1%-10% of cholesterol ester, 0.1%-10% of cholesterol, 0.1%-10% of antioxidant and 0.1%-5% of cellular activity regulator.

The triglyceride, the squalane, and the antioxidant are each heated and mixed at 70° C. to complete dissolution for preparing a first mixed raw material. The wax and ester, the free fatty acid, the phospholipid, the cholesterol ester, and the cholesterol are heated and mixed at 70° C. to complete dissolution for preparing a second mixed raw material. The first mixed raw material and the second mixed raw material are subjected to uniform mixing/stirring and cooling to 40-50° C. At this time, cellular activity regulator is added, followed by uniform mixing/stirring and cooling down to room temperature to obtain the artificial sebum film, wherein the heating temperature may also be set at 60-90° C.

For the triglyceride, triglyceride can be used or triglyceride derivatives may be used as a substitute. For the squalane, squalane can be used or squalane derivatives may be used as a substitute. For the cholesterol ester, cholesterol ester can be used or cholesterol ester derivatives may be used as a substitute.

In addition, for the antioxidant, Taiwan camellia seed oil is used; for the wax and ester, lanolin is used; for the free fatty acid, palmitic acid is used; for the phospholipid, lecithin is used; for the cholesterol ester, lanosterol ester is used; for the cellular activity regulator, adenosine triphosphate is used. The antioxidant may also be selected from either one of the camellia seed oil, vitamin E complex, vitamin C complex, wheat germ oil and unsaturated fatty acid or a combination of more than two, wherein the vitamin E complex refers to vitamin E or its derivatives, and the vitamin C complex refers to vitamin C or its derivatives. The cellular activity regulator may also be selected from either one of the adenosine triphosphate and algae extract or the combination of the two.

The difference between the artificial sebum film of the invention and the commonly known techniques lies mainly in the lower content of the triglyceride in order to reduce the negative effects of oxidation likelihood and the free fatty acid release. In addition, increasing the proportion of squalane in the composition may counteract the rapid loss of squalane in harsh environment, and may also help restore the skin in highly polluted environment to normal equilibrium state. Furthermore, lecithin is added as the phospholipid to coat the periphery of the artificial sebum film to form liposome having a sphere of 0.025 μm to 3.5 μm, so that the artificial sebum film can be rapidly and deeply permeated and delivered into the skin to achieve the effect of filling the skin barrier.

The artificial sebum film of the invention is additionally added with camellia seed oil (using exclusive Taiwan camellia seed oil) as the highly effective antioxidant to reduce lipid oxidation and effectively prolong the preservation period of artificial sebum film. In particular, in the field of anti-oxidation, it has been reported in the literature that camellia seed oil comprises rich antioxidant components such as catechins, chlorophyll, saponins, vitamin A, vitamin E, and unsaturated fatty acid and the like, and thus has the effect of scavenging free radicals. Further, clinical medicine pointed out that the camellia seed oil can reduce the chance of vascular embolism, and has effects of anti-aging, regulating blood lipids and blood sugar, relaxing the bowels, and liver protection etc. In the field of nutrition, it has the reputation of "plant gold" and comprises about 0.5% squalene, which can promote blood circulation, activate body function cells, reduce inflammation and sterilization, repair cells, and accelerate wound healing. The artificial sebum film of the invention is further added with adenosine triphosphate as the cellular active substance, so as to induce the cells to generate adenosine triphosphate by themselves and promote the cell respiration, thereby enhancing the function of cell metabolism and helping restore the skins in the highly polluted environment to the normal equilibrium state.

The artificial sebum film of the invention not only has skin moisturizing effect, but also has the functions of high anti-oxidation, high permeability to assist the skin in the highly polluted environment to restore to the normal sebum composition. Moreover, it combines with rapid and in-depth permeation technology of liposome to achieve the benefits of both replenishing intercellular lipid and constructing complete sebum film system.

While the invention has been described in terms of preferred embodiments, those skilled in the art will recognize that the invention can be practiced with modifications within the spirit and scope of the appended claims.

What is claimed is:

1. An artificial sebum film comprising, in raw material component and relative ratio, 2%-78.4% of triglyceride, 1%-15% of wax and ester, 20%-35% of squalane, 0.1%-7% of free fatty acid, 0.1%-6% of phospholipid, 0.1%-10% of cholesterol ester, 0.1%-10% of cholesterol, 0.1%-10% of antioxidant, and 0.1%-5% of cellular activity regulator;

wherein the antioxidant comprises one of camellia seed oil, vitamin E complex, vitamin C complex, wheat germ oil, and unsaturated fatty acid or a combination of more than two; the vitamin E complex is vitamin E or its derivatives; the vitamin C complex is vitamin C or its derivatives; the cellular activity regulator comprises either one of the adenosine triphosphate and algae extract or a combination of the two; the triglyceride is triglyceride or its derivatives; the squalane is squalane or its derivatives; and the cholesterol ester is cholesteryl ester or its derivatives.

* * * * *